US012648794B2

(12) United States Patent
Imai et al.

(10) Patent No.: US 12,648,794 B2
(45) Date of Patent: Jun. 9, 2026

(54) CELL TRANSPLANTING KIT, CELL TRANSPLANTING DEVICE, AND METHOD FOR TAKING IN TRANSPLANT

(71) Applicants: TOPPAN INC., Tokyo (JP); NATIONAL UNIVERSITY CORPORATION YOKOHAMA NATIONAL UNIVERSITY, Yokohama (JP); KANAGAWA INSTITUTE OF INDUSTRIAL SCIENCE AND TECHNOLOGY, Ebina (JP)

(72) Inventors: Keiichi Imai, Tokyo (JP); Junji Fukuda, Yokohama (JP); Tatsuto Kageyama, Yokohama (JP); Ayaka Nanmo, Yokohama (JP)

(73) Assignees: TOPPAN INC, Tokyo (JP); NATIONAL UNIVERSITY CORPORATION YOKOHAMA NATIONAL UNIVERSITY, Yokohama (JP); KANAGAWA INSTITUTE OF INDUSTRIAL SCIENCE AND TECHNOLOGY, Ebina (JP)

( * ) Notice: Subject to any disclaimer, the term of this patent is extended or adjusted under 35 U.S.C. 154(b) by 692 days.

(21) Appl. No.: 18/117,325

(22) Filed: Mar. 3, 2023

(65) Prior Publication Data

US 2023/0210557 A1      Jul. 6, 2023

Related U.S. Application Data

(63) Continuation of application No. PCT/JP2021/032659, filed on Sep. 6, 2021.

(30) Foreign Application Priority Data

Sep. 7, 2020      (JP) ................................. 2020-149874

(51) Int. Cl.
*A61B 17/34* (2006.01)
*A61B 17/00* (2006.01)
(Continued)

(52) U.S. Cl.
CPC .......... *A61B 17/3468* (2013.01); *A61L 27/38* (2013.01); *A61L 27/52* (2013.01);
(Continued)

(58) Field of Classification Search
CPC ...... A61B 17/3468; A61B 2017/00752; A61B 2017/00969; A61B 2017/306; A61F 2/10; A61F 2/105; A61L 27/52
See application file for complete search history.

(56) References Cited

U.S. PATENT DOCUMENTS

2009/0280469 A1      11/2009      Jujiwara et al.
2011/0313429 A1      12/2011      Anderson et al.
(Continued)

FOREIGN PATENT DOCUMENTS

JP      2008-029331 A      2/2008
JP      2013-526300 A      6/2013
(Continued)

OTHER PUBLICATIONS

International Search Report mailed Nov. 22, 2021, for International Application No. PCT/JP2021/032659, with English translation, 5 pages.
(Continued)

*Primary Examiner* — Majid Jamialahmadi
(74) *Attorney, Agent, or Firm* — Squire Patton Boggs (US) LLP

(57) ABSTRACT

A cell transplanting kit includes a transplant including a cell group and a cell transplanting device. The cell transplanting device includes a needle-shaped portion that extends in a shape of a tube, and an aspiration portion configured to
(Continued)

aspirate an interior of the needle-shaped portion. The needle-shaped portion is configured to attract the transplant by aspiration by the aspiration portion and take the transplant into the interior. The aspiration portion is configured to create an aspiration pressure in a range of −100 kPa to −0.1 kPa. The transplant includes a protection portion in a form of a gel covering at least a part of the cell group. The transplant has an outer diameter that is greater than or equal to a minimum value of the inner diameter of the needle-shaped portion. The protection portion has a jelly strength of greater than or equal to 100 g.

12 Claims, 8 Drawing Sheets

(51) Int. Cl.
 A61L 27/38        (2006.01)
 A61L 27/52        (2006.01)
(52) U.S. Cl.
 CPC .............. *A61B 2017/00752* (2013.01); *A61B 2017/00969* (2013.01)

(56)                    References Cited

U.S. PATENT DOCUMENTS

| | | |
|---|---|---|
| 2014/0037592 A1 | 2/2014 | Toyoshima et al. |
| 2014/0106432 A1 | 4/2014 | Fujiwara et al. |
| 2015/0238214 A1 | 8/2015 | Anderson et al. |
| 2016/0015424 A1* | 1/2016 | Kim ................... A61B 17/3468 |
| | | 606/187 |
| 2016/0160185 A1 | 6/2016 | Fujiwara et al. |
| 2018/0140316 A1 | 5/2018 | Anderson et al. |
| 2019/0062687 A1 | 2/2019 | Fukuda et al. |
| 2020/0222678 A1 | 7/2020 | Kodama et al. |
| 2020/0360039 A1 | 11/2020 | Anderson et al. |

FOREIGN PATENT DOCUMENTS

| | | |
|---|---|---|
| WO | WO 2012/108069 A1 | 8/2012 |
| WO | WO 2017/073625 A1 | 5/2017 |
| WO | WO 2019/064653 A1 | 4/2019 |

OTHER PUBLICATIONS

Notice of Reasons for Refusal dated Aug. 19, 2024, for Japanese Patent Application No. 2020-149874, with English translation, 8 pages.

* cited by examiner

CELL TRANSPLANTING KIT, CELL TRANSPLANTING DEVICE, AND METHOD FOR TAKING IN TRANSPLANT

CROSS-REFERENCE

This application is a continuation of International Patent Application No. PCT/JP2021/032659, filed Sep. 6, 2021, which claims the benefit of and priority to Japanese Patent Application No. 2020-149874, filed Sep. 7, 2020, the contents of all of which are hereby incorporated by reference in their entireties for all purposes.

BACKGROUND

The present disclosure relates to a cell transplanting kit, a cell transplanting device, and a method for taking in a transplant.

Technologies for transplanting cell groups into living bodies have been increasingly used. For example, attempts have been made to regenerate hair by culturing a group of cells that contribute to the formation of hair follicles, which are organs that produce hair, and intradermally transplanting the cell group. For successful hair regeneration, the transplanted cell groups desirably produce hair follicles that have normal tissue structures and the ability to produce healthy hair. Various researches and developments have been conducted on methods for producing cell groups capable of forming such hair follicles (refer to, for example, WO2017/073625, WO2012/108069, Japanese Patent Application Publication No. 2008-29331).

When transplanting a cell group, the handling of the cell group may apply an external force to the cell group. For example, when the cell group comes into contact with a tool for transferring the cell group from the culture vessel into a living body, the cell group receives a pressing force from the tool. When such an external force has a large effect on the cell group, a variation of the cell group, such as collapsing of the cell group, may occur, lowering the efficiency and the success rate of the transplant.

SUMMARY

An objective of the present disclosure is to provide a cell transplanting kit, a cell transplanting device, and a method for taking in a transplant that protect a cell group from an external force caused by the handling of the transplant.

In order to achieve the foregoing objective, a cell transplanting kit includes a transplant including a cell group and a cell transplanting device configured to place the transplant in a living body. The cell transplanting device includes a needle-shaped portion that extends in a shape of a tube and has an opening in a distal end portion of the needle-shaped portion, and an aspiration portion configured to aspirate an interior of the needle-shaped portion. The needle-shaped portion is configured to attract the transplant by aspiration by the aspiration portion and take the transplant into the interior through the opening, and is configured to, in a state in which the transplant has been taken in, have an inner diameter that is larger at a distal end of the needle-shaped portion and is reduced at a location between the distal end and a proximal end of the needle-shaped portion. The aspiration portion is configured to create an aspiration pressure in a range of −100 kPa to −0.1 kPa. The transplant includes a protection portion in a form of a gel covering at least a part of the cell group. The transplant has an outer diameter that is greater than or equal to a minimum value of the inner diameter of the needle-shaped portion. The protection portion has a jelly strength of greater than or equal to 100 g.

According to the above configuration, the protection portion covers the cell group. Thus, the cell group is protected from an external force applied to the transplant due to contact between the cell transplanting device and the transplant. This limits the occurrence of variation such as collapsing of the cell group. When the aspiration pressure is within the above range, the transplant is attracted to the needle-shaped portion by the aspiration and taken into the needle-shaped portion while limiting the deformation of the transplant.

In order to achieve the foregoing objective, a cell transplanting device is configured to place a transplant in a living body. The transplant includes a cell group and a protection portion in a form of a gel covering at least a part of the cell group. The cell transplanting device includes a needle-shaped portion including an outer tubular portion extending in a shape of a tube and having an opening in a distal end portion of the outer tubular portion and an inner tubular portion extending in a shape of a tube inside the outer tubular portion, and an aspiration portion configured to aspirate an interior of the inner tubular portion. The needle-shaped portion is configured to hold the transplant on a distal end portion of the inner tubular portion by aspiration by the aspiration portion and take the transplant into an interior of the needle-shaped portion through the opening. The aspiration portion is configured to create an aspiration pressure in a range of −100 kPa to −0.1 kPa.

According to the above configuration, the protection portion covers the cell group. Thus, the cell group is protected from an external force applied to the transplant due to contact between the cell transplanting device and the transplant. This limits the occurrence of variation such as collapsing of the cell group. When the aspiration pressure is within the above range, the transplant is held at the distal end portion of the inner tubular portion by the aspiration and taken into the needle-shaped portion while limiting the deformation of the transplant.

In order to achieve the foregoing objective, a method for taking a transplant into a cell transplanting device for placing the transplant in a living body is provided. The transplant includes a cell group and a protection portion in a form of a gel covering at least a part of the cell group. The cell transplanting device includes a needle-shaped portion extending in a shape of a tube and having an opening in a distal end portion of the needle-shaped portion, and an aspiration portion that aspirates an interior of the needle-shaped portion. The method includes attracting the transplant to the needle-shaped portion by aspiration by the aspiration portion and taking the transplant into the interior through the opening such that an aspiration pressure P (kPa) created by the aspiration portion and a jelly strength I (g) of the protection portion satisfy a following expression (1).

$$-1.0 \leq P/I \tag{1}$$

The above method limits the occurrence of variation such as collapsing of the cell group when the transplant is taken into the cell transplanting device using aspiration.

DESCRIPTION OF EXEMPLARY EMBODIMENTS

Referring to FIGS. 1 to 12, a cell transplanting kit, a cell transplanting device, and a method for taking in a transplant according to one embodiment will now be described. As used herein, the phrase "at least one of A and B" should be understood to refer to "only A, or only B, or both A and B."

The cell transplanting kit of the present embodiment includes a transplant and a cell transplanting device used for transferring and placing the transplant in a living body. A transplant target region in a living body is at least one of intracutaneous and subcutaneous, or within tissues of an organ, for example. In the present embodiment, the term "living body" encompasses not only bodies and tissues of living organisms, but also biological models, which are artificial products mimicking bodies and tissues of living organisms. In other words, the cell transplanting device of the present embodiment is capable of transferring and placing a transplant into a biological model, as well as transferring and placing a transplant into a living organism. The transplant, the cell transplanting device, and the method for taking in a transplant are now described in turn.

Transplant

Figure 1:
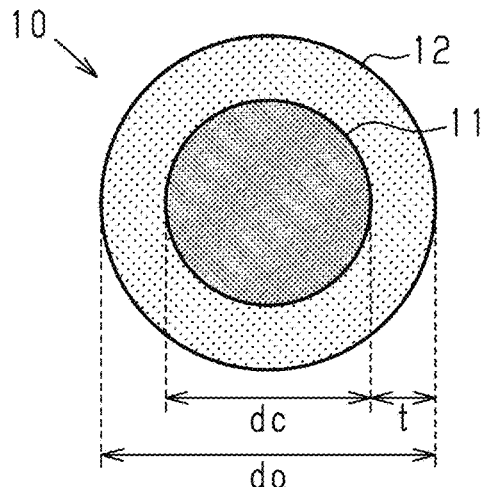
FIG. 1 is a diagram showing an example of a transplant in a cell transplanting kit of an embodiment.

As shown in FIG. 1, a transplant 10 includes a cell group 11 and a protection portion 12 covering the cell group 11.

The cell group 11 includes multiple cells. The cell group 11 may be a cluster of aggregated cells, or a cluster of cells bound by cell junctions. Alternatively, the cell group 11 may be formed by dispersed cells. Also, the cells forming the cell group 11 may be undifferentiated cells or differentiated cells, and the cell group 11 may include both undifferentiated cells and differentiated cells. The cell group 11 may be a cell cluster (spheroid), germ, tissue, organ, organoid, small organ, or the like.

The cell group 11 has the ability to act on tissue formation in a living body when placed in a transplant target region in the living body. One example of a cell group 11 with this ability is a cell aggregate having cells with sternness.

For example, when placed intracutaneously or subcutaneously, the cell group 11 contributes to hair growth or hair restoration. This cell group 11 has the ability to function as a hair follicle organ, the ability to differentiate into a hair follicle organ, the ability to induce or promote the formation of a hair follicle organ, or the ability to induce or promote hair formation in a hair follicle, for example. The cell group 11 may include cells that contribute to regulate hair colors, such as pigment cells or stem cells that differentiate into pigment cells. Furthermore, the cell group 11 may include vascular cells.

A specific example of the cell group 11 of the present embodiment is a hair follicle germ, which is a primitive hair follicle organ. A hair follicle germ includes mesenchymal cells and epithelial cells. In a hair follicle organ, a hair papilla cell, which is a mesenchymal cell, induces the differentiation of an epithelial hair follicle stem cell, and hair is formed by repeated division of hair matrix cells in the hair bulb thus formed. Hair follicle germs are cell groups that differentiate into these hair follicle organs.

For example, a hair follicle germ may be formed by mixing and culturing mesenchymal cells derived from mesenchymal tissues, such as hair papilla, and epithelial cells derived from epithelial tissues located in the bulge region, hair bulb base, and the like under predetermined conditions. However, the method for producing hair follicle germs is not limited to the above example. Also, there is no limitation to the origins of the mesenchymal cells and epithelial cells used for the production of hair follicle germs, and these cells may be cells derived from hair follicle organs, cells derived from organs other than hair follicle organs, or cells induced by pluripotent stem cells.

The protection portion 12 is a gel composition, specifically, hydrogel.

The main component of the protection portion 12 is a hydrophilic polymer. The hydrophilic polymer in the protection portion 12 may be a naturally-derived polymer, an artificially synthesized polymer, or a mixture of a naturally-derived polymer and an artificially synthesized polymer. Among these, a naturally-derived polymer is preferable. The hydrophilic polymer in the protection portion 12 is preferably a polymer having biocompatibility. A polymer having biocompatibility refers to a polymer that does not cause reactions such as serious inflammation when coming into contact with a living body. From these points of view, the hydrophilic polymer in the protection portion 12 is most preferably an extracellular matrix. Any type of substance that can function as an extracellular matrix in vivo may be used as a material for the protection portion 12.

Specific examples of the naturally-derived polymer in the material of the protection portion 12 include collagen (such as type I, type II, type III, type IV, type V, and type VI), carboxymethylcellulose, fibronectin, laminin, elastin, glycosaminoglycan, proteoglycan, fibrin, gelatin, agar, agarose, and sodium alginate. Specific examples of artificially synthesized polymers include polyacrylamide, polyvinyl alcohol, methylcellulose, and polyethylene oxide. Examples of the products that may be used as a material of the protection portion 12 include Matrigel (manufactured by Corning Incorporated, registered trademark), Cell Matrix (manufactured by Nitta Gelatin Inc., registered trademark), and Mebiol Gel (IKEDA SCIENTIFIC Co., Ltd., manufactured by Mebiol Inc., registered trademark). As for the above materials, one type of material may be used alone, or different types of materials may be mixed to be used.

Among the materials described above, type I collagen is preferably used as a material of the protection portion 12. The type I collagen may be human-derived or non-human animal-derived. Examples of non-human animals are pigs, cows, horses, and chickens.

The strength of the protection portion 12 is represented by jelly strength specified in JIS K6503. The jelly strength of the protection portion 12 is preferably greater than or equal to 100 g. When the jelly strength of the protection portion 12 is greater than or equal to 100 g, the protection portion 12 protects the cell group 11 in a favorable manner. To increase the protection function, the jelly strength of the protection portion 12 is preferably greater than or equal to 150 g. There is no limitation to the upper limit of the jelly strength of the protection portion 12, but the jelly strength of the protection portion 12 is preferably less than or equal to 300 g to facilitate the formation of the protection portion 12.

The jelly strength of the protection portion 12 can be adjusted by adjusting the type and the composition of the materials of the protection portion 12. For example, when collagen is used as a material of the protection portion 12, the concentration of the collagen solution used to form the protection portion 12 is preferably greater than or equal to 1.5 mg/ml, more preferably greater than or equal to 2.0 mg/m, to obtain a jelly strength of greater than or equal to 100 g.

The protection portion 12 may include a promoting factor for promoting the growth and engraftment of the cell group 11. Examples of promoting factors include insulin, EGF, FGF, IGF, N-2 supplement and RevitaCell supplement manufactured by Thermo Fisher Scientific, RSPO1, Noggin, ROCK-inhibitor (such as Y27632, HA-1077), GSK-3β inhibitor (such as SB-216763, BIO, CHIR99021, CHIR98014, TWS119), anti-inflammatory agents (such as dexamethasone, prednisolone, methylprednisolone, triamicinolone, betamethasone, cortisol, acetylsalicylic acid, ibuprofen, loxoprofen, diclofenac), PD0325901, RepSox, PluriSln #1, and TNF-α. The protection portion 12 may include only one type of the above promoting factors, or may include two or more types of promoting factors.

The protection portion 12 may also include an antibiotic to limit the propagation of bacteria.

The protection portion 12 may be colorless and transparent, or may be colored. When the protection portion 12 is colorless and transparent, the cell group 11 can be easily observed while the transplant 10 is being formed. When the protection portion 12 is colored, the visibility of the transplant 10 is enhanced, so that the position of the transplant 10 can be easily identified when the transplant 10 is taken into or released from the cell transplanting device.

The protection portion 12 covering the cell group 11 protects the cell group 11 from an external force applied to the transplant 10. To enhance the protection function of the protection portion 12, the protection portion 12 preferably covers the entire cell group 11. However, as long as the protection portion 12 covers at least a part of the cell group 11, the cell group 11 is protected from an external force as compared with a configuration in which the whole cell group 11 is not covered by the protection portion 12.

In the transplant 10, the cell group 11 may be one cluster, or may be divided into multiple clusters. When the cell group 11 is formed by dispersed cells, the cells are dispersed in the protection portion 12. The transplant 10 may include dispersed cells in addition to an aggregated cell group 11.

When the cell group 11 is used to contribute to hair growth or hair restoration, the cell group 11 may be cultured such that one aggregated cell group 11 corresponds to one hair follicle organ, and transplant may be conducted such that one transplant 10 is placed at a position where one hair follicle organ develops. In this manner, the distribution of growing hairs can be easily controlled. That is, in the transplant 10, the cell group 11 is preferably one aggregate. When the cell group 11 is a hair follicle germ, the cell group 11 is one aggregate in the transplant 10.

When the cell group 11 is one aggregate, the outer diameter dc of the cell group 11 may be in a range of 50 μm to 1000 μm, for example. To reduce the burden required for culturing the cell group 11 and to increase the engraftment rate of the cell group 11, the outer diameter dc is preferably in a range of 100 μm to 800 μm. The outer diameter dc of the cell group 11 is the diameter of a sphere obtained by approximating the cell group 11 to a sphere, that is, the diameter of the smallest sphere circumscribing the cell group 11.

The outer diameter do of the transplant 10 may be greater than 50 μm and less than or equal to 3 mm, for example. The outer diameter do of the transplant 10 depends on the size of the cell group 11 and the thickness of the protection portion 12. The outer diameter do of the transplant 10 is the diameter of a sphere obtained by approximating the transplant 10 to a sphere, that is, the diameter of the smallest sphere circumscribing the transplant 10.

When the cell group 11 is one aggregate, the thickness t of the protection portion 12 is the length from the surface of the cell group 11 to the surface of the protection portion 12 in the direction of the diameter of the smallest sphere circumscribing the transplant 10. The thickness t of the protection portion 12 may be determined according to the level of protection function required for the protection portion 12. A greater thickness t enhances the function of the protection portion 12 in protecting the cell group 11. To facilitate the growth of the cell group 11 by ensuring the oxygen permeability and the nutrient permeability of the protection portion 12, the thickness t is preferably less than or equal to the outer diameter dc of the cell group 11.

Around the cell group 11, the thickness t may be uniform or non-uniform. For example, when different sections of the cell group 11 differ in strength, the section of the protection portion 12 that covers a section of the cell group 11 with a lower strength may have a thickness t that is greater than the thickness t of the other section. This allows the section of the cell group 11 with a lower strength to receive intensive protection.

The outer diameter do of the transplant 10 is measured by observing the entire transplant 10 with a microscope. When the protection portion 12 is transparent, the boundary between the cell group 11 and the protection portion 12 can be identified by transmission observation, allowing the outer diameter dc of the cell group 11 and the thickness t of the protection portion 12 to be measured through observation using a microscope.

When the cell group 11 is an aggregate of cells forming a cluster, the cell group 11 may be shaped to spread isotropically from its center like a sphere, or shaped to spread anisotropically from its center.

Figure 2:
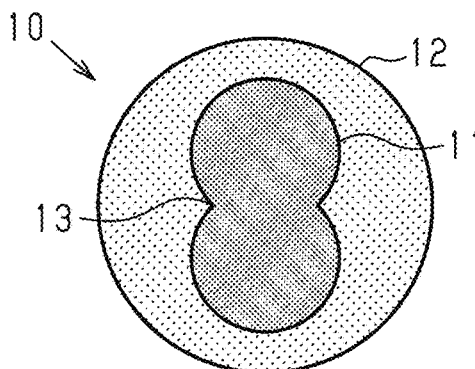
FIG. 2 is a diagram showing an example of a transplant in the cell transplanting kit of the above embodiment.

For example, as shown in FIG. 2, the cell group 11 may have the shape of two substantially spherical clusters joined together, and have a constricted central section. The constricted section is a constricted portion 13. In a hair follicle germ, a section in which mesenchymal cells aggregate is formed next to a section in which epithelial cells aggregate. Thus, when the cell group 11 is a hair follicle germ, the cell group 11 may have a shape in which a constricted central section is at the boundary between these aggregated sections.

In the example shown in FIG. 2, the thickness t of the protection portion 12 is not uniform, and the thickness t increases in the section covering the constricted portion 13. The cell group 11 with the constricted portion 13 has a lower strength at the constricted portion 13 and is thus susceptible to being collapsed by an external force at the constricted portion 13. Since the thickness t of the protection portion 12 is large at the position corresponding to the constricted portion 13, an external force is less likely to impact the constricted portion 13. The cell group 11 is thus properly protected.

Even when the cell group 11 has an uneven shape, the outer diameter dc of the cell group 11 is the diameter of the smallest sphere circumscribing the cell group 11.

Figure 3:
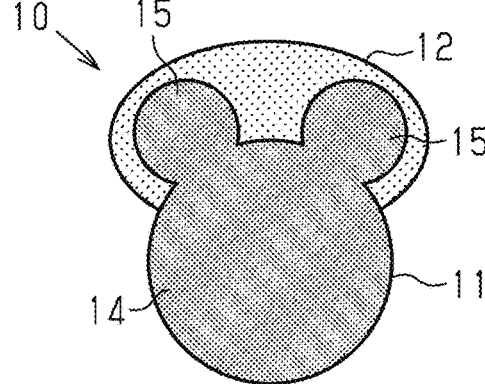
FIG. 3 is a diagram showing an example of a transplant in the cell transplanting kit of the above embodiment.

FIG. 3 shows an example in which the cell group 11 has the shape of one large cluster to which two small clusters are joined. A section corresponding to the large cluster is a large cluster portion 14, and the sections corresponding to the small clusters are small cluster portions 15. The two small cluster portions 15 are next to each other.

In the example shown in FIG. 3, the protection portion 12 covers the cell group 11 only around the two small cluster portions 15 and does not cover the entire cell group 11. While the whole of the two small cluster portions 15 and the boundary between the large cluster portion 14 and the small cluster portions 15 are covered with the protection portion 12, a part of the large cluster portion 14 is exposed from the protection portion 12.

The cell group 11 with the large cluster portion 14 and the small cluster portions 15 has lower strength around the small cluster portions 15, including in the boundary between the large cluster portion 14 and the small cluster portions 15. Thus, the cell group 11 is susceptible to being collapsed by an external force around the small cluster portions 15. However, since the protection portion 12 covers the small cluster portions 15 and the boundary between the large cluster portion 14 and the small cluster portions 15, the cell group 11 is properly protected.

Even when the transplant 10 has an uneven shape, the outer diameter do of the transplant 10 is the diameter of the smallest sphere circumscribing the transplant 10.

There is no limitation to the method for forming the transplant 10. In other words, there is no limitation to the method for covering the cell group 11 with the protection portion 12. For example, the transplant 10 may be formed by suspending cells in a hydrogel that serves as the protection portion 12 to form the cell group 11 in the hydrogel, by applying a hydrogel that serves as the protection portion 12 to the cell group 11, or by enclosing the cell group 11 with a hydrogel that serves as the protection portion 12.

In addition to the cell group 11 and the protection portion 12, the transplant 10 may include a member that assists in the placement of the cell group 11 in a living body.

Cell Transplanting Device

Figure 4:
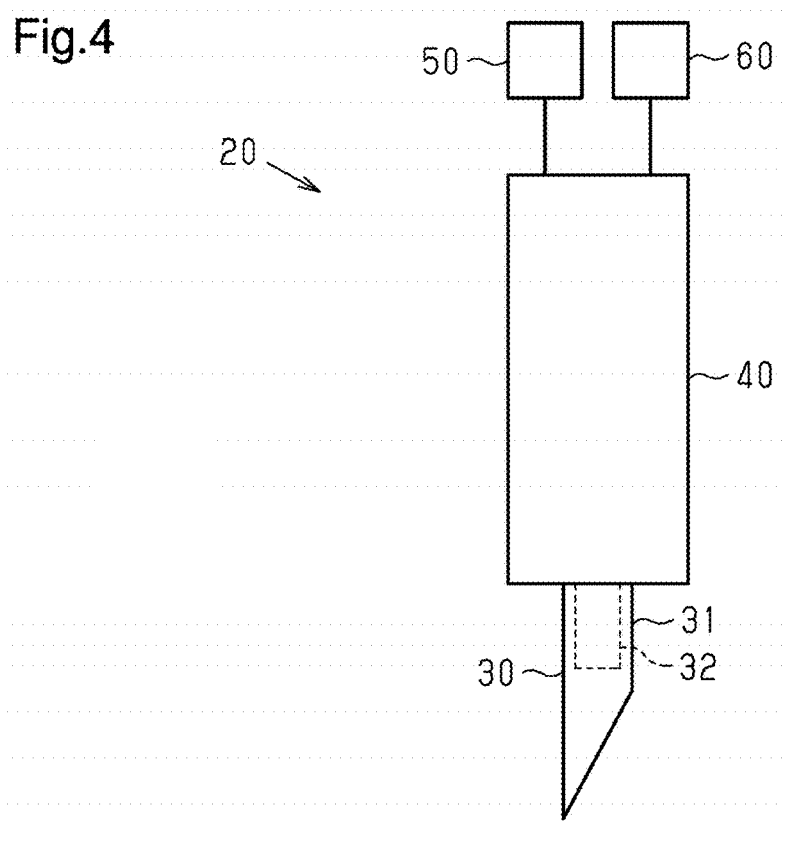
FIG. 4 is a diagram showing the configuration of a cell transplanting device of the above embodiment.

As shown in FIG. 4, a cell transplanting device 20 includes a needle-shaped portion 30 extending in one direction and a support portion 40 supporting the needle-shaped portion 30. The needle-shaped portion 30 has an outer tubular portion 31 extending in the shape of a tube and an inner tubular portion 32 extending in the shape of a tube inside the outer tubular portion 31. That is, the needle-shaped portion 30 has the shape of a double-layered tube.

Provided that the distal end portion of the outer tubular portion 31 is shaped to pierce a transplant site of a living body, there is no limitation to the shape of the other portion of the outer tubular portion 31. For example, the outer tubular portion 31 extends in the shape of a cylinder, and the distal end portion of the outer tubular portion 31 is cut obliquely with respect to the direction in which the cylinder extends, and is thus sharp.

There is no limitation to the shape of the inner tubular portion 32 as long as it is tubular. For example, when the outer tubular portion 31 has the shape of a cylinder, the inner tubular portion 32 may also have the shape of a cylinder. The end surface of the distal end portion of the inner tubular portion 32 is preferably a plane perpendicular to the direction in which the inner tubular portion 32 extends.

The support portion 40 may be formed integrally with the outer tubular portion 31 or may be a member formed separately from the outer tubular portion 31. There is no limitation to the outer shape of the support portion 40. When the support portion 40 is formed integrally with the outer tubular portion 31, the outer tubular portion 31 projects from the support portion 40.

When the support portion 40 is a member formed separately from the outer tubular portion 31, the support portion 40 surrounds the outside of the section of the outer tubular portion 31 excluding the distal end portion and its vicinity, and supports the outer tubular portion 31. For example, the needle-shaped portion 30 extends through the hole of the support portion 40, and thus the needle-shaped portion 30 is coupled to the support portion 40. The distal end portion of the outer tubular portion 31 and its vicinity project from the support portion 40 in the direction in which the needle-shaped portion 30 extends.

Regardless of whether the outer tubular portion 31 and the support portion 40 are separate members or integrally formed, the section of the outer tubular portion 31 projecting from the support portion 40 includes at least a part that is to advance to a transplant target region in a living body. The outer tubular portion 31, the inner tubular portion 32, and the support portion 40 are made of metal or plastic. The outer tubular portion 31 is made of a material that is strong enough to pierce a transplant site of a living body.

The cell transplanting device 20 further includes an aspiration portion 50, which aspirates the interior of the needle-shaped portion 30, and a position change portion 60, which includes a mechanism for moving the inner tubular portion 32 relative to the outer tubular portion 31 in the direction in which the needle-shaped portion 30 extends.

The aspiration portion 50 has a mechanism for aspirating air by movement of a piston, a pump, or the like. The aspiration portion 50 is connected to the inner tubular portion 32 and aspirates the interior of the inner tubular portion 32. The aspiration portion 50 may be incorporated inside the support portion 40, or may be provided outside the support portion 40 and extended through the support portion 40 to be connected to the inner tubular portion 32.

When the position change portion 60 is actuated, the inner tubular portion 32 is moved relative to the outer tubular portion 31 between a position at which the distal end portion of the inner tubular portion 32 is placed within the outer tubular portion 31 and a position at which the distal end portion of the inner tubular portion 32 projects from the opening 33 in the distal end portion of the outer tubular portion 31. A state in which the distal end portion of the inner tubular portion 32 is within the outer tubular portion 31 is a first state of the needle-shaped portion 30, and a state in which the distal end portion of the inner tubular portion 32 projects from the opening 33 is a second state of the needle-shaped portion 30.

The position change portion 60 includes members for pushing and pulling the outer and inner tubular portions 31 and 32. The position change portion 60 may be operated manually. Alternatively, the position change portion 60 may include an electronic component such as a motor, and the position change portion 60 may be electrically operated. The position change portion 60 may be incorporated inside the support portion 40, or may be provided outside the support portion 40 and extended through the support portion 40 to be connected to the outer tubular portion 31 and the inner tubular portion 32.

In addition to the portions described above, the cell transplanting device 20 may have a member for determining the depth at which the transplant 10 is positioned in the transplant site. For example, the cell transplanting device 20 may have a stopper or a scale for regulating the depth of penetration of the needle-shaped portion 30 into the transplant site.

Figure 5:
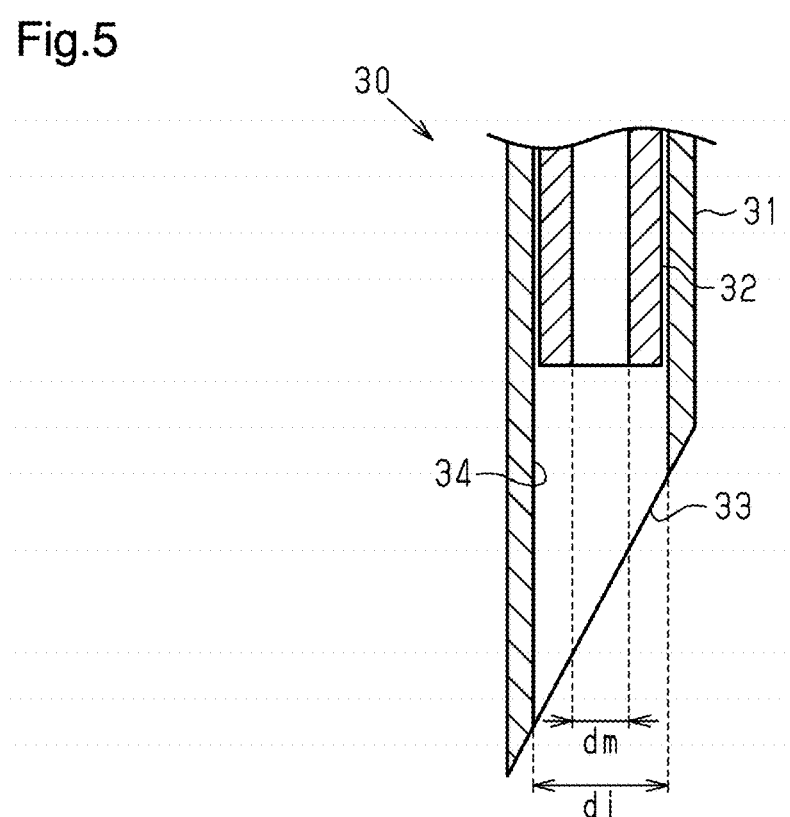
FIG. 5 is a diagram showing the cross-sectional structure of a needle-shaped portion of the cell transplanting device of the above embodiment.

Referring to FIG. 5, the internal structure of the needle-shaped portion 30 is further described. In the first state in which the distal end portion of the inner tubular portion 32 is positioned inside the outer tubular portion 31, the tubular section between the distal end of the inner tubular portion 32 and the distal end of the outer tubular portion 31 is an accommodation portion 34, which accommodates the transplant 10. The accommodation portion 34 communicates with the opening 33 of the outer tubular portion 31.

An accommodation diameter di is the inner diameter of the outer tubular portion 31, that is, the inner diameter of the accommodation portion 34. An aspiration diameter dm is the inner diameter of the inner tubular portion 32. The aspiration diameter dm is smaller than the accommodation diameter di. To facilitate the formation of the outer and inner tubular portions 31 and 32, each of the accommodation diameter di and the aspiration diameter dm is preferably greater than or equal to 20 μm.

In the first state, the inner diameter of the needle-shaped portion 30 changes from the accommodation diameter di to the aspiration diameter dm. In other words, in the first state, the inner diameter of the needle-shaped portion 30 is larger at the distal end and is reduced at a location between the distal end and the proximal end of the needle-shaped portion 30. The outer diameter do of the transplant 10 described above is greater than or equal to the aspiration diameter dm and less than or equal to 2.5 times the accommodation diameter di.

When the inner diameter of the outer tubular portion 31 is not uniform, the accommodation diameter di is the inner diameter of the distal end of the accommodation portion 34. Also, when the inner diameter of the inner tubular portion 32 is not uniform, the aspiration diameter dm is the inner diameter of the distal end of the inner tubular portion 32. When the inner diameter of the inner tubular portion 32 is uniform, the aspiration diameter dm is the minimum value of the inner diameter of the needle-shaped portion 30. For smooth formation and assembly of the outer and inner tubular portions 31 and 32, the inner diameters of the outer and inner tubular portions 31 and 32 are preferably uniform, and the accommodation portion 34 and the inner tubular portion 32 are preferably cylindrical.

Transplant Capturing

Figure 6:
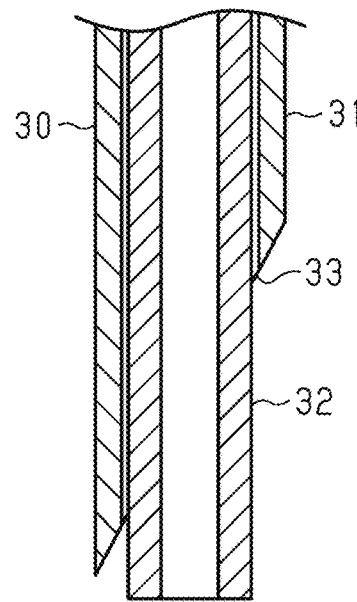
FIG. 6 is a diagram showing the needle-shaped portion before holding a transplant in a method for taking in a transplant of the above embodiment.
Figure 7:
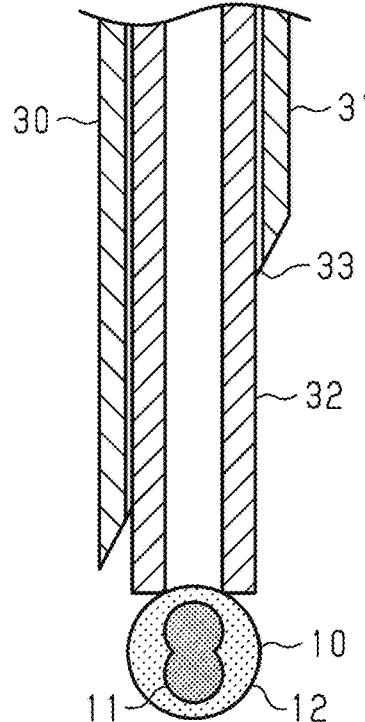
FIG. 7 is a diagram showing a state in which a transplant is held at the distal end portion of an inner tubular portion of the needle-shaped portion in the method for taking in a transplant of the above embodiment.
Figure 8:
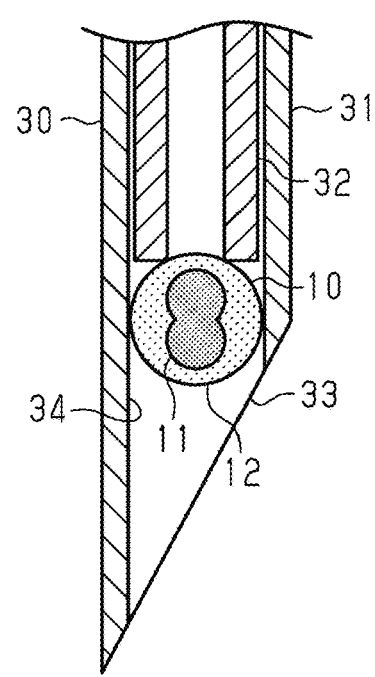
FIG. 8 is a diagram showing a state in which the transplant is taken in the interior of the needle-shaped portion in the method for taking in a transplant of the above embodiment.

Referring to FIGS. 6 to 8, a method for taking the transplant 10 into the cell transplanting device 20 is described.

As shown in FIG. 6, first, the needle-shaped portion 30 is set in the second state in which the distal end portion of the inner tubular portion 32 projects from the opening 33 in the distal end portion of the outer tubular portion 31. Then, the distal end portion of the needle-shaped portion 30 in the second state, that is, the distal end portion of the inner tubular portion 32 is positioned near the transplant 10 placed in a tray such as a culture vessel.

As shown in FIG. 7, when the aspiration portion 50 is driven to aspirate the interior of the inner tubular portion 32, the transplant 10 is attracted to the inner tubular portion 32 and then held at the distal end portion of the inner tubular portion 32 in contact with the distal end of the inner tubular portion 32. The outer diameter do of the transplant 10 is larger than the aspiration diameter dm so that the transplant 10 does not enter the interior of the inner tubular portion 32. When the outer diameter do of the transplant 10 is greater than or equal to 2.8 times the aspiration diameter dm, the possibility of the transplant 10 entering the interior of the inner tubular portion 32 is reliably reduced.

As shown in FIG. 8, with the transplant 10 held at the distal end portion of the inner tubular portion 32, the position change portion 60 is actuated to move the inner tubular portion 32 relative to the outer tubular portion 31. This pulls the distal end portion of the inner tubular portion 32 and the transplant 10 into the outer tubular portion 31 through the opening 33. The needle-shaped portion 30 is thus placed in the first state, and the transplant 10 is accommodated in the accommodation portion 34. This completes the capturing of the transplant 10 into the needle-shaped portion 30.

The aspiration pressure P in the inner tubular portion 32 created by the aspiration portion 50 is set according to the size of the outer diameter do of the transplant 10 relative to the aspiration diameter dm to a degree that does not cause the transplant 10 to be pulled into the inner tubular portion 32 by the aspiration. When the outer diameter do of the transplant 10 is greater than or equal to 5.1 times the aspiration diameter dm, the transplant 10 is unlikely to be pulled into the inner tubular portion 32 of the transplant 10 even when the aspiration pressure P is as strong as −100 kPa.

In the present embodiment, the aspiration pressure P is in a range of −100 kPa to −0.1 kPa. That is, when the strongest aspiration force is used, the aspiration pressure P is −100 kPa, and when the weakest aspiration force is used, the aspiration pressure P is −0.1 kPa. The aspiration pressure P represents the magnitude of the strongest aspiration pressure from the start to the end of aspiration.

An aspiration pressure P of −0.1 kPa or stronger allows the transplant 10 to be attracted to and held at the distal end portion of the inner tubular portion 32. On the other hand, when the aspiration pressure P is too strong, the section of the transplant 10 facing the opening of the distal end portion of the inner tubular portion 32 may be squeezed into the opening, causing the transplant 10 to be deformed. The deformation may remain in the transplant 10 as an aspiration mark after the aspiration is stopped. The aspiration mark indicates that strong stress remains in the transplant 10, and such stress may lead to a variation of the cell group 11 such as cell death. An aspiration pressure P of −100 kPa or weaker limits the formation of an aspiration mark in the transplant 10. To limit the formation of an aspiration mark in a further suitable manner, the aspiration pressure P is preferably greater than or equal to −80 kPa.

When the protection portion 12 is a gel of an extracellular matrix, the function of protecting the cell group 11 is obtained such that the transplant 10 is less likely to collapse when attracted to the distal end portion of the inner tubular portion 32 by the aspiration with an aspiration pressure P within the above range.

In particular, the protection portion 12 having a jelly strength I of greater than or equal to 100 g reliably reduces the possibility of the transplant 10 collapsing when attracted to the inner tubular portion 32 with an aspiration pressure P within the above range. That is, when the aspiration pressure P (kPa) and the jelly strength I (g) of the protection portion 12 are set such that the aspiration pressure P and the jelly strength I satisfy the following Expression (1), the possibility of the transplant 10 collapsing when held by the inner tubular portion 32 using aspiration is reliably reduced.

$$-1.0 \leq P/I \qquad (1)$$

Since the transplant 10 has flexibility, the transplant 10 having an outer diameter do that is greater than the accommodation diameter di can still be taken into the accommodation portion 34 through the opening 33, provided that the outer diameter do is less than or equal to 2.5 times the accommodation diameter di. When the outer diameter do of the transplant 10 is greater than the accommodation diameter di, the transplant 10 rubs against the inner surface of the outer tubular portion 31 as the transplant 10 is moved into the accommodation portion 34 and removed from the accommodation portion 34 in the living body. However, the protection portion 12 covering the cell group 11 limits the collapsing of the transplant 10 due to the rubbing. When the jelly strength I of the protection portion 12 is greater than or equal to 100 g, the possibility of the transplant 10 collapsing due to the rubbing is further reduced.

The larger the outer diameter do of the transplant 10, the more cells the cell group 11 can have. A greater number of cells facilitates the growth and engraftment of the transplanted cell group 11. Moreover, a greater outer diameter do of the transplant 10 allows the protection portion 12 to be thicker, increasing the protection function. At the same time, the needle-shaped portion 30 with a smaller outer diameter is easier to pierce a living body with and reduces the burden on the living body when the needle-shaped portion 30 advances. A smaller accommodation diameter di allows for a smaller outer diameter of the needle-shaped portion 30, that is, the outer diameter of the outer tubular portion 31. For this reason, to increase the ease of insertion of the needle-shaped portion 30 into a living body and to reduce the burden on the living body, a smaller accommodation diameter di is preferable.

When the outer diameter do of the transplant 10 is greater than 1.0 times and less than or equal to 2.5 times the accommodation diameter di, the transplant 10 having a relatively large outer diameter do can be transplanted without increasing the accommodation diameter di, as compared with a configuration in which the outer diameter do is smaller than the accommodation diameter di. As a result, it is possible to improve the ease of insertion of the needle-shaped portion 30 into a living body and to reduce the burden on the living body, as well as to facilitate the growth and engraftment of the cell group 11. When the needle-shaped portion 30 is to be inserted into the skin, to improve the ease of insertion of the needle-shaped portion 30 into a living body and reduce the burden on the living body, the outer diameter of the outer tubular portion 31 is preferably less than or equal to 600 μm.

When the outer diameter do of the transplant 10 is larger than the accommodation diameter di, to pull the transplant 10 into the accommodation portion 34 with the transplant 10 held at the distal end portion of the inner tubular portion 32, the aspiration pressure P is preferably increased when the outer diameter do of the transplant 10 is larger in relation to the accommodation diameter di.

On the other hand, when the outer diameter do of the transplant 10 is smaller than the accommodation diameter di, the transplant 10 is less likely to rub against the inner surface of the outer tubular portion 31 as the transplant 10 is taken in or released. This reduces the load on the transplant 10.

Protection liquid, which is a liquid material for protecting the transplant 10, may be taken into the needle-shaped portion 30 from a tray such as a culture vessel together with the transplant 10. The protection liquid may include physiological saline and nutrients, for example.

Placement of Transplant in Living Body

Figure 9:
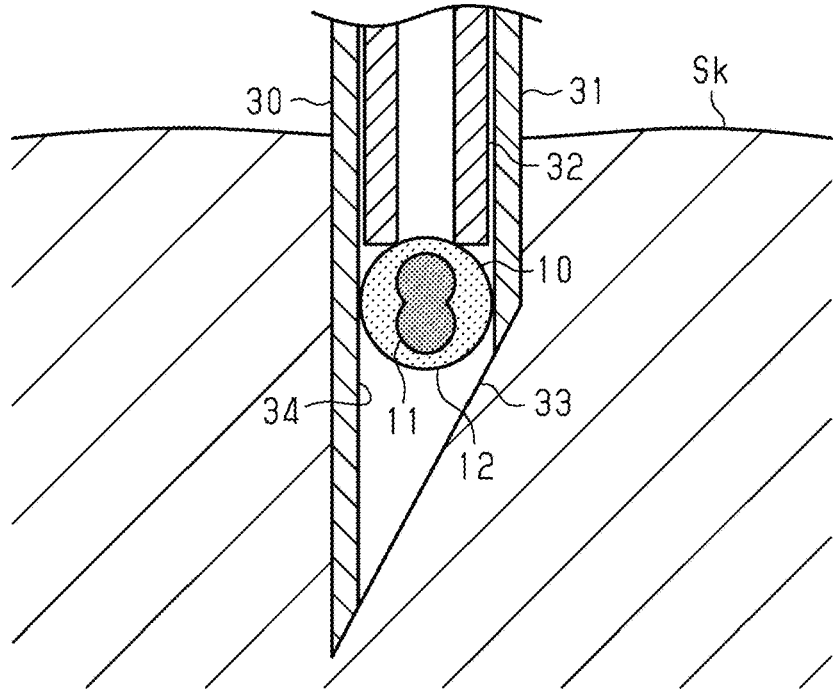
FIG. 9 is a diagram showing a state in which the needle-shaped portion pierces a living body in a method for placing a transplant of the above embodiment.
Figure 10:
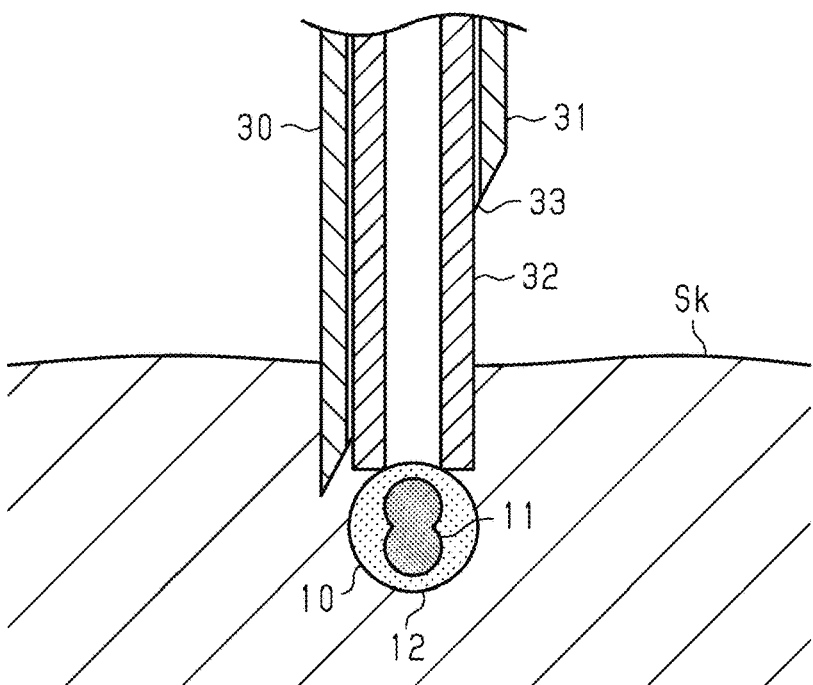
FIG. 10 is a diagram showing a state in which the inner tubular portion has moved relative to the outer tubular portion in the method for placing a transplant of the above embodiment.
Figure 11:
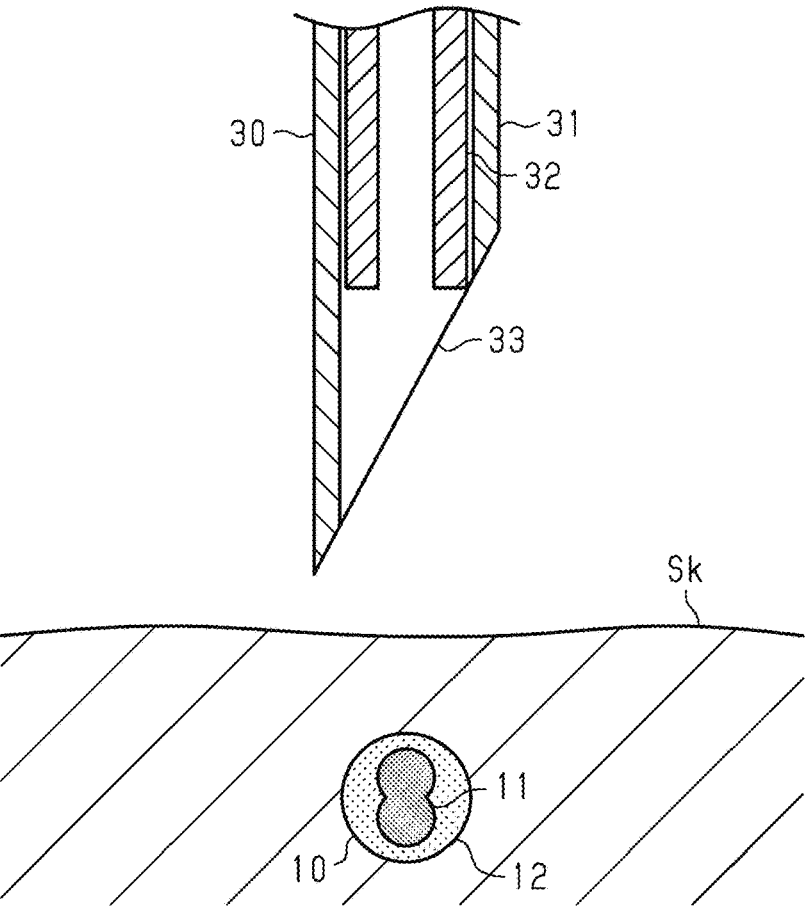
FIG. 11 is a diagram showing a state in which the needle-shaped portion has been pulled out from the living body in the method for placing a transplant of the above embodiment.

Referring to FIGS. 9 to 11, a method for placing the transplant 10 in a living body is now described.

Once the transplant 10 is taken into the needle-shaped portion 30, the cell transplanting device 20 is transferred to a transplant site Sk, which may be the skin of the head, of a living body with the transplant 10 accommodated in the accommodation portion 34, that is, with the needle-shaped portion 30 in the first state.

Then, as shown in FIG. 9, the needle-shaped portion 30 pierces the transplant site Sk. At this time, the distal end portion of the outer tubular portion 31 is located at the distal end portion of the cell transplanting device 20. Since the distal end portion of the outer tubular portion 31 is shaped to easily pierce a living body, the needle-shaped portion 30 smoothly enters the transplant site Sk. The needle-shaped portion 30 may be advanced into the transplant site Sk in a direction perpendicular to the surface of the transplant site Sk, or may be advanced into the transplant site Sk in a direction inclined to the surface of the transplant site Sk.

As shown in FIG. 10, when the distal end portion of the outer tubular portion 31 reaches the transplant target region, the position change portion 60 is actuated to move the inner tubular portion 32 relative to the outer tubular portion 31, bringing the needle-shaped portion 30 into the second state. As a result, together with the distal end portion of the inner tubular portion 32, the transplant 10 moves out through the opening 33 of the outer tubular portion 31. Then, the aspiration by the aspiration portion 50 is stopped, releasing the transplant 10 from the inner tubular portion 32, and the transplant 10 is placed in the transplant target region.

To bring the needle-shaped portion 30 into the second state, the outer tubular portion 31 may be retracted in the direction in which the needle-shaped portion 30 is pulled out from the transplant site Sk, or the inner tubular portion 32 may be further advanced in the transplant site Sk without changing the position of the outer tubular portion 31. To reduce the load on the transplant 10, the outer tubular portion 31 is preferably retracted, leaving the distal end portion of the inner tubular portion 32 and the transplant 10 in the space that was previously occupied by the distal end portion of the outer tubular portion 31 in the transplant site Sk. This reduces the likelihood that the transplant 10 is pressed by the surrounding tissues and thus receives a load when moving out of the outer tubular portion 31. Also, since the protection portion 12 covers the cell group 11, any load applied to the transplant 10 when the transplant 10 is placed in the living body has a limited effect on the cell group 11.

When protection liquid has been taken into the needle-shaped portion 30 together with the transplant 10, the protection liquid may also be released to the transplant target region. Furthermore, the aspiration portion 50 may be configured to apply pressure to the inner tubular portion 32 in addition to performing aspiration so that air is sent into the inner tubular portion 32 when the transplant 10 is released.

As shown in FIG. 11, once the transplant 10 is placed in the transplant target region, the inner tubular portion 32 is moved into the outer tubular portion 31, and the needle-shaped portion 30 is pulled out from the transplant site Sk. This completes the placement of the transplant 10 in the living body. Alternatively, after the placement of the transplant 10, the needle-shaped portion 30 may be pulled out while in the second state without moving the inner tubular portion 32.

Modifications

The needle-shaped portion 30 is not limited to a configuration including the outer and inner tubular portions 31 and 32 and may have any configuration in which the inner diameter of the needle-shaped portion 30 is larger at the distal end of the needle-shaped portion 30 and is reduced at a location between the distal end and the proximal end of the needle-shaped portion 30 in a state in which the transplant 10 is accommodated. For example, as shown in FIG. 12, the needle-shaped portion 30 may be a single tubular structure having an inner diameter that changes at a location along the needle-shaped portion 30.

Figure 12:
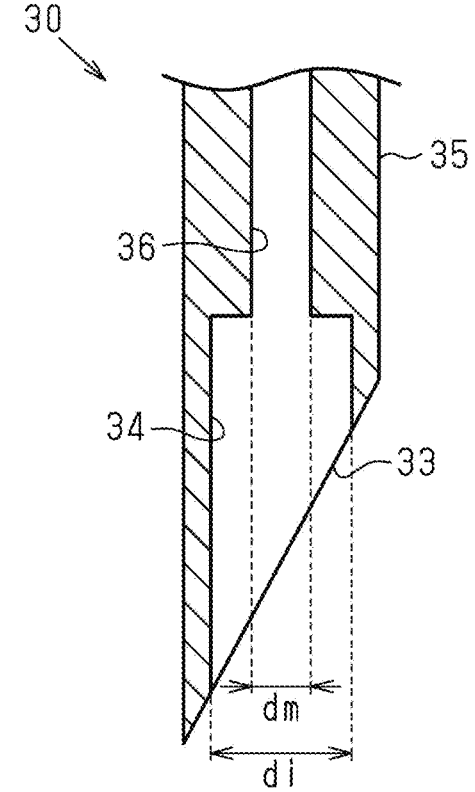
FIG. 12 is a diagram showing the cross-sectional structure of a needle-shaped portion of a modification.

In the example shown in FIG. 12, the needle-shaped portion 30 is formed by a tubular portion 35 having the shape of a tube with multiple stages. The tubular portion 35 has an accommodation portion 34, which communicates with an opening 33 in the distal end portion, and a small diameter portion 36, which has an inner diameter smaller than the inner diameter of the accommodation portion 34. The small diameter portion 36 is located at the side of the accommodation portion 34 where the proximal end of the tubular portion 35 is located. The accommodation diameter di is the inner diameter of the accommodation portion 34, and the aspiration diameter dm is the inner diameter of the small diameter portion 36.

The aspiration portion 50 aspirates the interior of the tubular portion 35, causing the transplant 10 to be pulled into the tubular portion 35 through the opening 33 and accommodated in the accommodation portion 34.

FIG. 12 illustrates a configuration in which the inner diameter of the needle-shaped portion 30 changes at a certain location from the accommodation diameter di to the aspiration diameter dm, so that the inner side of the needle-shaped portion 30 has a step. However, the inner diameter of the needle-shaped portion 30 may change gradually.

When the outer diameter do of the transplant 10 is greater than or equal to the minimum value of the inner diameter of the needle-shaped portion 30, the transplant 10 accommodated in the interior of the needle-shaped portion 30 is in contact with the needle-shaped portion 30 at least at the section where the inner diameter is smallest. Although the transplant 10 receives an external force due to the contact with the needle-shaped portion 30, the protection portion 12 covering the cell group 11 protects the cell group 11 from the external force.

When the aspiration pressure P created by the aspiration portion 50 is in a range of −100 kPa to −0.1 kPa and the outer diameter do of the transplant 10 is less than or equal to 2.5 times the accommodation diameter di, the transplant 10 can be taken into the needle-shaped portion 30 while limiting the collapsing of the transplant 10.

When the needle-shaped portion 30 includes the outer and inner tubular portions 31 and 32, the inner tubular portion 32 does not have to be moved relative to the outer tubular portion 31 and may remain inside the outer tubular portion 31. In this case, when the aspiration portion 50 aspirates the interior of the inner tubular portion 32, the transplant 10 is pulled into the outer tubular portion 31 through the opening 33 and accommodated in the accommodation portion 34.

The cell transplanting kit may include the material for forming the protection portion 12, and the step of preparing the transplant 10 having the protection portion 12 covering the cell group 11 through the formation of the protection portion 12 may be performed by the user of the cell transplanting kit. That is, the cell transplanting kit may include, together with the cell transplanting device 20, the transplant 10 in which the protection portion 12 having a jelly strength of greater than or equal to 100 g covers at least a part of the cell group 11. Alternatively, the cell transplanting kit may include, together with the cell transplanting device 20, the material for forming the protection portion 12 so that the protection portion 12 having a jelly strength of greater than or equal to 100 g can be formed around the cell group 11.

Furthermore, in addition to the transplant 10 and the cell transplanting device 20, the cell transplanting kit may include a tray for holding the transplant 10. The tray may be the culture vessel used to culture the cell group 11, or may be a container different from the culture vessel, and the cell group 11 may be transferred from the culture vessel to the tray. Also, the transplant 10 may be formed in the tray, or the transplant 10 formed in another container may be transferred to the tray.

The tray preferably has holding areas for transplants 10, which may be recesses, and each holding area preferably holds one transplant 10. Thus, by aligning the needle-shaped portion 30 of the cell transplanting device 20 with a holding area of the tray, a transplant 10 can be efficiently taken into the needle-shaped portion 30.

The cell transplanting device 20 may include multiple needle-shaped portions 30. The cell transplanting device 20 having multiple needle-shaped portions 30 can collectively transplant multiple transplants 10. In this case, the aspiration by the aspiration portion 50 may be performed collectively for the multiple needle-shaped portions 30, or may be performed independently for each needle-shaped portion 30, provided that the aspiration pressure P for each needle-shaped portion 30 is in a range of −100 kPa to −0.1 kPa.

The cell group 11 in the transplant 10 does not have to be a cell group that contributes to hair growth or hair restoration, and may be a cell group that has a desired effect when placed in tissues of a living body. For example, the cell group 11 may be a cell group that has cosmetic effects, such as the removal of skin wrinkles or improvement of moisture condition.

EXAMPLES

The above-described cell transplanting kit and the method for taking in a transplant are described using specific examples and comparative examples.

Examples

Transplant

A cell suspension containing human hair papilla cells (C-12071, manufactured by PromoCell GmbH) and a collagen solution (Cellmatrix Type I-A, manufactured by Nitta Gelatin Inc.) with a concentration of 2.4 mg/ml was supplied to each well of a round bottom 96-well plate and left to stand at 37° C. for 5 minutes to harden the collagen. Then, a human hair papilla cell growth medium (C-26501, manufactured by PromoCell GmbH) was added, and the cells were cultured in the above wells for 3 days at 37° C. in an environment of 5% $CO_2$ concentration. Cell clusters were thus formed in the collagen. As a result, transplants were obtained each having a cell group as a cell cluster covered with a protection portion made of collagen.

The size of the outer diameter of the formed transplant can be changed by changing the amount of cell suspension supplied to each well. Also, the outer diameter of the cell group and the thickness of the protection portion can be adjusted by adjusting the ratio of the cells to the collagen solution in the cell suspension. Specifically, the number of cells supplied to each well was $5 \times 10^3$ to evaluate the aspiration pressure described below. To evaluate the outer diameter of the transplant described below, 63 patterns between $5 \times 10^3$ cells and $20 \times 10^3$ cells were used.

Figure 13:
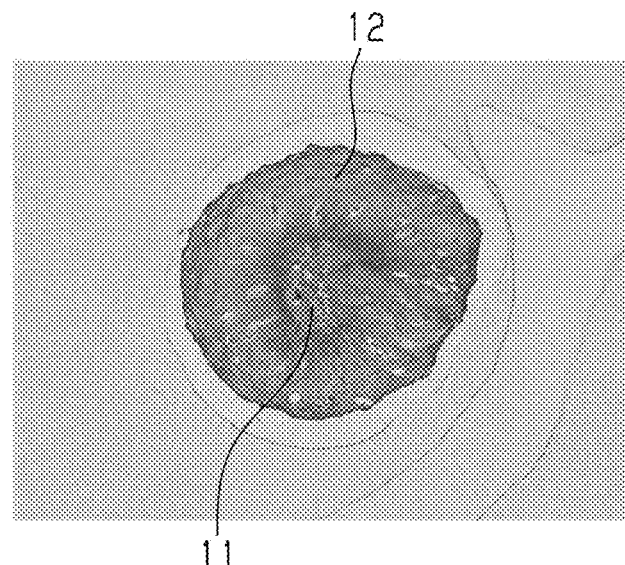
FIG. 13 is a diagram showing an image of a stained cross-section of a transplant of an example.
Figure 14:
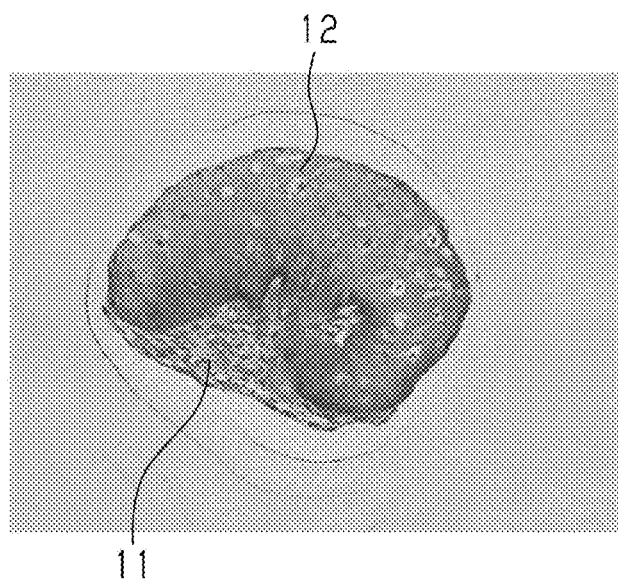
FIG. 14 is a diagram showing an image of a stained cross-section of a transplant of an example.
Figure 15:
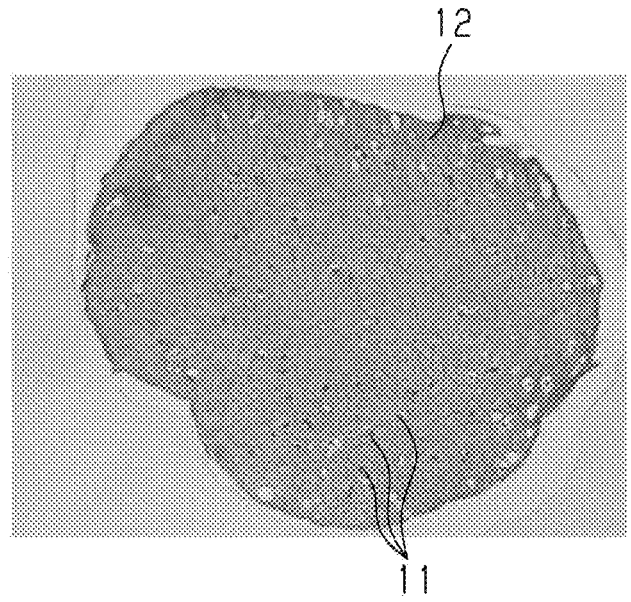
FIG. 15 is a diagram showing an image of a stained cross-section of a transplant of an example.

FIGS. 13 to 15 show cross-sectional images of transplants obtained by Masson's Trichrome staining of sections prepared from transplants formed with protection portions. In FIG. 13, the protection portion 12 covers the whole of the aggregated cell group 11. In FIG. 14, the protection portion 12 covers a part of the aggregated cell group 11. In FIG. 15, the cells forming the cell group 11 are dispersed in the protection portion 12.

Whether the cell group forms an aggregated cluster in the transplant can be controlled by adjusting the balance between the number of cells and the amount of the protection portion, taking into account the migration property and aggregability of the cells. Specifically, cells of a type with low migration property tend to disperse in the protection portion, whereas cells of a type that easily aggregate tend to form a cell cluster in the protection portion. When the number of cells is small with respect to the amount of the protection portion, the interaction between cells is weak, and thus the cells are less likely to aggregate. As a result, the formed transplant is more likely to have cells dispersed in the protection portion.

Cell Transplanting Device

A cell transplanting device including a needle-shaped portion having an outer tubular portion and an inner tubular portion was prepared. The outer tubular portion is a 25 G needle. That is, the accommodation portion of the outer tubular portion is cylindrical and has a uniform inner diameter of 400 μm. The outer tubular portion is made of stainless steel (SUS304). The inner tubular portion has the shape of a cylinder, and the end surface of the distal end portion of the inner tubular portion is a plane perpendicular to the direction in which the inner tubular portion extends. The inner tubular portion has a uniform outer diameter of 360 μm and a uniform inner diameter of 170 μm. The inner tubular portion is made of stainless steel (SUS304). The inner tubular portion is configured to be movable relative to the outer tubular portion, and an aspiration portion including a pump mechanism is connected to the proximal end of the inner tubular portion.

Accordingly, in the cell transplanting device of the example, the accommodation diameter di is 400 μm, the aspiration diameter dm is 170 μm, and the aspiration diameter dm is the minimum value of the inner diameter of the needle-shaped portion. The cross-sectional shape of the outer tubular portion is circular with an inner diameter of 400 μm as described above, and the arithmetic mean roughness Ra of the inner surface of the outer tubular portion is 400 nm. The moving speed of the inner tubular portion relative to the outer tubular portion is set to 1.5 mm/s.

Comparative Example

Transplant

To each well of a round bottom 96-well plate, $5 \times 10^3$ human hair papilla cells (C-12071, manufactured by PromoCell GmbH) and a hair papilla cell growth medium (C-26501, manufactured by PromoCell GmbH) were supplied, and the human hair papilla cells were cultured for 3 days in an environment of 37° C. and a $CO_2$ concentration of 5%. Cell clusters were thus formed. The transplant of the comparative example consists only of a cell group as a cell cluster, and the cell group is not covered with a protection portion.

Cell Transplanting Device

As a cell transplanting device of the comparative example, a device having the same configuration as the cell transplanting device of the example was used.

Transplant Handling Test

The transplants of the example and the comparative example were tested as follows to check the presence or absence of variation in the transplants caused by the handling for transplanting. As for the example, the outer diameter of the transplant was about 600 μm and the jelly strength of the protection portion in the transplant was about 150 g. As for the comparative example, the outer diameter of the transplant was about 600 μm.

First, the interior of the inner tubular portion of the needle-shaped portion in the second state of the cell transplanting device was aspirated with an aspiration pressure of −5 kPa to hold the transplant at the distal end portion of the inner tubular portion. Then, the inner tubular portion and the transplant were pulled into the outer tubular portion to bring the needle-shaped portion into the first state, and the transplant was taken into the needle-shaped portion. Then, the needle-shaped portion was brought into the second state again, and the aspiration was stopped to release the transplant into a petri dish from the needle-shaped portion. The released transplant was observed using an inverted microscope.

Figure 16:
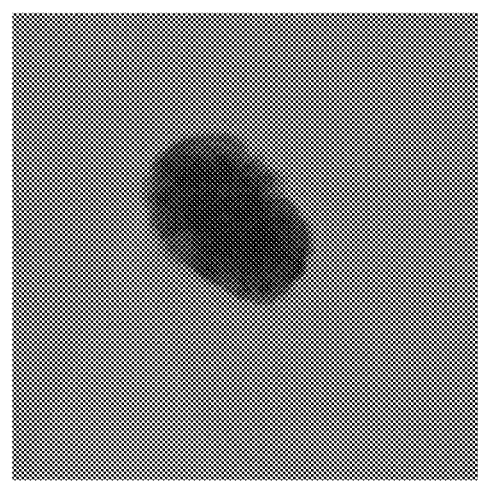
FIG. 16 is a diagram showing an external image of a transplant of an Example released after being taken into the cell transplanting device.
Figure 17:
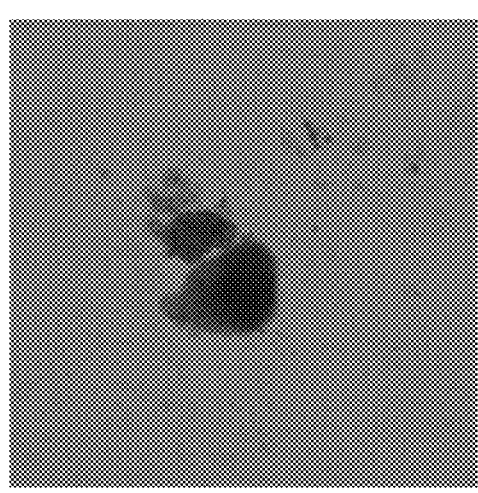
FIG. 17 is a diagram showing an external image of a transplant of a comparative example released after being taken into the cell transplanting device.

FIG. 16 shows an image of a transplant of the example after release, and FIG. 17 shows an image of a transplant of the comparative example after release. As shown in FIGS. 16 and 17, the transplant of the example with the protection portion did not collapse, whereas the transplant of the comparative example without the protection portion collapsed and was divided. From this result, it was ascertained that covering the cell group with the protection portion protects the cell group.

Evaluation of Aspiration Pressure

Different aspiration pressures were applied to transplants of the example to observe whether the transplants collapsed in the following manner. The outer diameter of the transplant was about 580 μm, and the jelly strength of the protection portion in each transplant was about 150 g. The aspiration pressure was set to −19 kPa, −32 kPa, −52 kPa, and −71 kPa, and the following tests were performed for each aspiration pressure.

The interior of the inner tubular portion of the needle-shaped portion in the second state of the cell transplanting device was aspirated with a set aspiration pressure to hold the transplant at the distal end portion of the inner tubular portion. Then, the inner tubular portion and the transplant were pulled into the outer tubular portion to bring the needle-shaped portion into the first state, and the transplant was thus taken into the needle-shaped portion. After 5 seconds had elapsed since the transplant was taken into the needle-shaped portion, the needle-shaped portion was brought into the second state again and the aspiration was stopped, thereby releasing the transplant from the needle-shaped portion into a petri dish. The released transplant was observed using an inverted microscope.

As a result of observation of the released transplants, no collapsing was found in the transplants at any aspiration pressure. It was therefore ascertained that any aspiration pressure within the above range allows the transplant to be taken into and released from the needle-shaped portion without collapsing.

At any aspiration pressure, the transplant was held on the distal end of the inner tubular portion, the transplant did not enter the interior of the inner tubular portion, and the formation of aspiration marks on the transplant was not observed. Additionally, the same test as above was performed on a transplant of the example having an outer diameter of about 900 μm and by setting the aspiration pressure to −100 kPa. The test did not find entry of the transplant into the inner tubular portion, formation of aspiration marks, or collapsing of the transplant.

Evaluation of Outer Diameter of Transplant

As described below, transplants of the examples having different outer diameters were prepared to observe whether it was possible to take these transplants into the needle-shaped portion and whether the transplants collapsed.

First, 63 transplants with different outer diameters were prepared. Of these transplants, the minimum outer diameter was 486 μm, and the maximum outer diameter was 1378 μm. The jelly strength of the protection portion of each transplant was about 150 g. The following tests were performed on each transplant.

The interior of the inner tubular portion of the needle-shaped portion in the second state of the cell transplanting device was aspirated with an aspiration pressure of −50 kPa to hold the transplant at the distal end portion of the inner tubular portion. Then, the inner tubular portion and the transplant were pulled into the outer tubular portion to bring the needle-shaped portion into the first state, and it was checked whether the transplant was taken into the needle-shaped portion.

When the transplant was taken into the needle-shaped portion, the needle-shaped portion was brought into the second state again and the aspiration was stopped to release the transplant from the needle-shaped portion into a petri dish. The released transplant was observed using an inverted microscope.

Nine transplants with outer diameters of greater than or equal to 1086 μm were caught at the opening of the outer tubular portion and could not be taken into the needle-shaped portion. As for 54 transplants with outer diameters of less than or equal to 978 μm, the transplants were successfully taken into the needle-shaped portion. The observation on the released transplants found no collapsing of these transplants. It was therefore ascertained that when the outer diameter of the transplant is less than or equal to 2.5 times the accommodation diameter, the transplant can be taken into and released from the needle-shaped portion without collapsing.

As described in the embodiments and examples above, the cell transplanting kit, the cell transplanting device, and the method for taking in a transplant have the advantageous effects listed below.

(1) The protection portion 12 in the form of a gel covers the cell group 11. Thus, the cell group 11 is protected from an external force applied to the transplant 10 due to contact between the cell transplanting device 20 and the transplant 10. This limits the occurrence of variation such as collapsing of the cell group 11.

(2) The aspiration pressure P used to attract the transplant 10 to the needle-shaped portion 30 to take the transplant 10 into the needle-shaped portion 30 is in a range of −100 kPa to −0.1 kPa. This allows the transplant 10 to be attracted to the needle-shaped portion 30 by the aspiration and taken into the needle-shaped portion 30 while limiting the deformation of the transplant 10.

(3) When the jelly strength of the protection portion 12 is greater than or equal to 100 g, the cell group 11 is reliably protected. In particular, the possibility of collapsing of the transplant 10 is reliably reduced when the transplant 10 is attracted to the inner tubular portion 32 with an aspiration pressure P within the above range. Additionally, the possibility of collapsing of the transplant 10 caused by the transplant 10 rubbing against the inner surface of the outer tubular portion 31 is reliably reduced.

(4) The protection portion 12 including an extracellular matrix advantageously provides the function of protecting the cell group 11 and also allows the transplant 10 to be more suitable for placement in a living body. For example, the use of an extracellular matrix with the function of assisting bonding between cells as the protection portion 12 facilitates the engraftment of the transplant 10. Furthermore, when the protection portion 12 includes collagen, which is an extracellular matrix that is particularly abundant in the skin, the biocompatibility of the protection portion 12 is advantageously increased when the transplant 10 is transplanted in the skin.

(5) The outer diameter do of the transplant 10 is less than or equal to 2.5 times the accommodation diameter di of the accommodation portion 34. This allows the transplant 10 to be smoothly accommodated in the accommodation portion 34. Also, since the transplant 10 having an outer diameter do larger than the accommodation diameter di can be taken into the needle-shaped portion 30, the transplant 10 having a large outer diameter do can be transplanted without increasing the outer diameter of the needle-shaped portion 30. As a result, an improvement in the ease of insertion of the needle-shaped portion 30 into a living body, a reduction in the burden on the living body, and the promotion of the growth and engraftment of the cell group 11 are simultaneously achieved.

(6) Since the outer diameter do of the transplant 10 is greater than or equal to 2.8 times the aspiration diameter dm of the needle-shaped portion 30, the transplant 10 is held partway along the needle portion 30. Specifically, when the needle-shaped portion 30 includes the outer tubular portion 31 and the inner tubular portion 32, the transplant 10 is unlikely to move into the inner tubular portion 32. The transplant 10 is thus held at the distal end portion of the inner tubular portion 32. This allows the transplant 10 to be smoothly taken into and released from the needle-shaped portion 30.

(7) The needle-shaped portion 30 includes the outer and inner tubular portions 31 and 32, and the inner tubular portion 32 is movable relative to the outer tubular portion 31 in the direction in which the needle-shaped portion 30 extends. The aspiration portion 50 aspirates the interior of the inner tubular portion 32 with the distal end portion of the inner tubular portion 32 projecting from the opening 33 of the outer tubular portion 31, thereby holding the transplant 10 at the distal end portion of the inner tubular portion 32. Thus, the transplant 10 as the target to be taken in is reliably captured to be taken into the needle-shaped portion 30.

(8) The cell group 11 includes a hair follicle germ. A hair follicle germ has a structure in which a section where mesenchymal cells aggregate is formed next to a section where epithelial cells aggregate. Thus, a hair follicle germ often has a shape other than a substantially spherical shape. For this reason, the cell group 11 tends to have an area where the strength is locally low, so that the cell group 11 would be susceptible to being collapsed by an external force in the absence of the protection portion 12. Also, the cell group 11 loses its function as a germ when either of the section where mesenchymal cells aggregate or the section where the epithelial cells aggregate is destroyed. Accordingly, any collapsing of the cell group 11 significantly affects the function of the cell group 11 as compared with a configuration in which the cell group 11 is an aggregate of the same type of cells. The protection of the transplant 10 provided by the protection portion 12 is therefore particularly advantageous.

(9) The method for taking in the transplant 10 attracts the transplant 10 by aspiration caused by the aspiration portion 50 such that the aspiration pressure P (kPa) created by the aspiration portion 50 and the jelly strength I (g) of the protection portion 12 satisfy $-1.0 \leq P/I$ to take the transplant 10 into the interior through the opening 33 in the distal end portion of the needle-shaped portion 30. Thus, the possibility of collapsing of the transplant 10 resulting from the capturing of the transplant 10 by aspiration is reliably reduced.

(10) When the method for taking in the transplant 10 includes preparing the transplant 10 by forming the protection portion 12, the capturing of the transplant 10 that satisfies the above expression can be suitably achieved by adjusting the material of the protection portion 12, for example, in the step of preparing the transplant 10 to adjust the jelly strength I, and by adjusting the aspiration pressure P in the step of taking in the transplant 10.

ADDITIONAL STATEMENT

The means for solving the above problems includes the following technical concepts derived from the above embodiments.

A cell transplanting kit, including:

a material that can form a protection portion in a form of a gel covering at least a part of a cell group; and a cell transplanting device for placing a transplant including the cell group and the protection portion in a living body, wherein the cell transplanting device includes:

a needle-shaped portion that extends in a shape of a tube and has an opening in a distal end portion of the needle-shaped portion, and an aspiration portion configured to aspirate an interior of the needle-shaped portion, the needle-shaped portion is configured to attract the transplant by aspiration by the aspiration portion and take the transplant into the interior through the opening, and is configured to, in a state in which the transplant has been taken in, have an inner diameter that is larger at a distal end of the needle-shaped portion and is reduced at a location between the distal end and a proximal end of the needle-shaped portion, the aspiration portion is configured to create an aspiration pressure in a range of $-100$ kPa to $-0.1$ kPa, the transplant has an outer diameter that is greater than or equal to a minimum value of the inner diameter of the needle-shaped portion, and the protection portion has a jelly strength of greater than or equal to 100 g.

The above configuration allows for the formation of a transplant in which a cell group is covered with a protection portion. Thus, the cell group is protected from an external force applied to the transplant due to contact between the cell transplanting device and the transplant. This limits the occurrence of a variation such as collapsing of the cell group. When the aspiration pressure is within the above range, the transplant is attracted to the needle-shaped portion by the aspiration and taken into the needle-shaped portion while limiting the deformation of the transplant.

The invention claimed is:

1. A cell transplanting kit, comprising:

a transplant including a cell group; and a cell transplanting device configured to place the transplant in a living body, wherein the cell transplanting device includes:

a needle-shaped portion that extends in a shape of a tube and has an opening in a distal end portion of the needle-shaped portion; and an aspiration portion configured to aspirate an interior of the needle-shaped portion, the needle-shaped portion is configured to attract the transplant by aspiration by the aspiration portion and take the transplant into the interior through the opening, and is configured to, in a state in which the transplant has been taken in, have an inner diameter that is larger at a distal end of the needle-shaped portion and is reduced at a location between the distal end and a proximal end of the needle-shaped portion, the aspiration portion is configured to create an aspiration pressure in a range of −100 kPa to −0.1 kPa, the transplant includes a protection portion in a form of a gel covering at least a part of the cell group, the transplant has an outer diameter that is greater than or equal to a minimum value of the inner diameter of the needle-shaped portion, and the protection portion has a jelly strength of greater than or equal to 100 g.

2. The cell transplanting kit according to claim 1, wherein the needle-shaped portion has an accommodation portion that communicates with the opening and is configured to accommodate the transplant that is taken in, and the outer diameter of the transplant is less than or equal to 2.5 times an inner diameter of the accommodation portion.

3. The cell transplanting kit according to claim 1, wherein the outer diameter of the transplant is greater than or equal to 2.8 times the minimum value of the inner diameter of the needle-shaped portion.

4. The cell transplanting kit according to claim 1, wherein the protection portion includes an extracellular matrix.

5. The cell transplanting kit according to claim 1, wherein the protection portion includes collagen.

6. The cell transplanting kit according to claim 1, wherein the needle-shaped portion includes an outer tubular portion extending in a shape of a tube and having the opening, and an inner tubular portion extending in a shape of a tube inside the outer tubular portion, the inner tubular portion is configured to be movable relative to the outer tubular portion between a position at which a distal end portion of the inner tubular portion is located inside the outer tubular portion and a position at which the distal end portion of the inner tubular portion projects from the opening of the outer tubular portion, and the aspiration portion is configured to aspirate an interior of the inner tubular portion so that aspiration by the aspiration portion holds the transplant at the distal end portion of the inner tubular portion.

7. The cell transplanting kit according to claim 1, wherein the cell group includes a hair follicle germ.

8. The cell transplanting kit according to claim 1, wherein the needle-shaped portion includes an outer tubular portion extending in a shape of a tube and having the opening, and an inner tubular portion extending in a shape of a tube inside the outer tubular portion, the aspiration portion is configured to aspirate an interior of the inner tubular portion, the inner tubular portion is configured to be movable relative to the outer tubular portion between a first position at which a distal end portion of the inner tubular portion is located inside the outer tubular portion and a second position at which the distal end portion of the inner tubular portion projects from the opening of the outer tubular portion, the needle-shaped portion is configured to, by aspiration by the aspiration portion, attract the transplant together with a liquid material for protecting the transplant and hold the transplant outside the distal end portion such that the transplant is in contact with the distal end portion of the inner tubular portion, and to take the transplant into an interior through the opening of the outer tubular portion, which is the opening in a distal end portion of the needle-shaped portion, by setting the inner tubular portion being in the first position, the outer tubular portion has an accommodation portion that communicates with the opening and accommodates the transplant that is taken in, and the transplant has an outer diameter that is larger than an inner diameter of the distal end portion of the inner tubular portion and is larger than 1.0 times an inner diameter of the accommodation portion and less than or equal to 2.5 times the inner diameter of the accommodation portion.

9. The cell transplanting kit according to claim 1, wherein the needle-shaped portion includes a single tubular structure having an inner diameter that changes at a location along the needle-shaped portion.

10. The cell transplanting kit according to claim 9, wherein the needle-shaped portion is a single tubular structure including a first portion having a first inner diameter and a second portion having a second inner diameter, the second portion is located on a side of the first portion where a proximal end of the needle-shaped portion is located, and the second inner diameter is smaller than the first inner diameter, and an inner diameter of the needle-shaped portion changes from the first inner diameter to the second inner diameter at a certain location between a distal end and the proximal end of the needle-shaped portion.

11. A method for taking the transplant into the cell transplanting device using the cell transplanting kit according to claim 1 the method comprises attracting the transplant to the needle-shaped portion by aspiration by the aspiration portion and taking the transplant into the interior through the opening such that the aspiration pressure P (kPa) created by the aspiration portion and the jelly strength I (g) of the protection portion satisfy a following expression (1)

$$-1.0 \leq P/I \tag{1}.$$

12. The method for taking in a transplant according to claim 11, further comprising preparing the transplant by forming the protection portion.

* * * * *